(12) United States Patent
Weidenhaupt et al.

(10) Patent No.: US 8,343,074 B2
(45) Date of Patent: Jan. 1, 2013

(54) FLUID HANDLING DEVICES (75) Inventors: Klaus Peter Weidenhaupt, Inverness (GB); James Moffat, Inverness (GB); Sebastian Böhm, Inverness (GB)

(73) Assignee: LifeScan Scotland Limited, Inverness (GB)

( * ) Notice: Subject to any disclaimer, the term of this patent is extended or adjusted under 35 U.S.C. 154(b) by 232 days.

(21) Appl. No.: 10/883,026

(22) Filed: Jun. 30, 2004

(65) Prior Publication Data

US 2006/0004303 A1   Jan. 5, 2006

(51) Int. Cl.
*A61B 5/00* (2006.01)
(52) U.S. Cl. ...................................................... 600/583
(58) Field of Classification Search .................. 600/300, 600/301, 576, 573, 583–585; 606/181, 182, 606/184; 604/48
See application file for complete search history.

(56) References Cited

U.S. PATENT DOCUMENTS

| | | | |
|---|---|---|---|
| 3,123,066 A | 3/1964 | Brumley | |
| 3,136,310 A | 6/1964 | Meltzer | |
| 3,208,452 A | 9/1965 | Stern | |
| 3,338,239 A | 8/1967 | Mausteller | |
| 3,620,676 A | 11/1971 | Davis | |
| 3,640,267 A | 2/1972 | Hurtig et al. | |
| 3,958,560 A | 5/1976 | March | |
| 4,014,321 A | 3/1977 | March | |
| 4,088,448 A | 5/1978 | Lilia et al. | |
| 4,195,641 A | 4/1980 | Johnes et al. | |
| 4,200,110 A | 4/1980 | Peterson et al. | |
| 4,224,125 A | 9/1980 | Nakamura et al. | |
| 4,407,290 A | 10/1983 | Wilber | |
| 4,420,566 A | 12/1983 | Jessop et al. | |
| 4,426,451 A | 1/1984 | Columbus | |
| 4,480,685 A | 11/1984 | Gilbertson | |
| 4,489,974 A | 12/1984 | Warhol | |
| 4,517,978 A | 5/1985 | Levin | |
| 4,545,382 A | 10/1985 | Higgins et al. | |
| 4,622,974 A | 11/1986 | Coleman et al. | |
| 4,637,403 A | 1/1987 | Garcia et al. | |
| 4,648,408 A | 3/1987 | Hutcheson et al. | |
| 4,655,225 A | 4/1987 | Dähne et al. | |
| 4,660,971 A | 4/1987 | Sage et al. | |
| 4,685,463 A | 8/1987 | Williams | |
| 4,703,756 A | 11/1987 | Gough et al. | |
| 4,704,029 A | 11/1987 | Van Heuvelen | |
| 4,730,622 A | 3/1988 | Cohen | |
| 4,750,830 A | 6/1988 | Lee | |
| 4,756,884 A | 7/1988 | Hillman et al. | |
| 4,761,381 A | 8/1988 | Blatt et al. | |
| 4,784,577 A * | 11/1988 | Ritson et al. ................. | 417/219 |
| 4,805,623 A | 2/1989 | Jöbsis | |

(Continued)

FOREIGN PATENT DOCUMENTS

DE   3708031   11/1987

(Continued)

OTHER PUBLICATIONS

Ash et al., "A subcutaneous capillary filtrate collector for measurement of blood chemistries", ASAIO Journal, Jul.-Sep. 1993, 39 (3) Pm699-705.

(Continued)

*Primary Examiner* — Max Hindenburg
*Assistant Examiner* — Fangemonique Smith (57) ABSTRACT

Devices for determining the concentration of an analyte in a fluid are provided. Also provided are systems and kits for use in practicing the subject methods.

10 Claims, 4 Drawing Sheets

U.S. PATENT DOCUMENTS

| | | |
|---|---|---|
| 4,849,340 A | 7/1989 | Oberhardt |
| 4,866,129 A | 9/1989 | Brandstetter et al. |
| 4,868,129 A | 9/1989 | Gibbons et al. |
| 4,873,993 A | 10/1989 | Meserol et al. |
| 4,882,492 A | 11/1989 | Schlager |
| 4,883,068 A | 11/1989 | Dechow |
| 4,901,728 A | 2/1990 | Hutchison |
| 4,935,346 A | 6/1990 | Phillips et al. |
| 4,953,552 A | 9/1990 | DeMarzo |
| 4,954,318 A | 9/1990 | Yafuso et al. |
| 4,960,467 A | 10/1990 | Peck |
| 4,962,040 A | 10/1990 | Hugl et al. |
| 4,981,779 A | 1/1991 | Wagner |
| 5,002,054 A | 3/1991 | Ash et al. |
| 5,014,718 A | 5/1991 | Mitchen |
| 5,026,388 A | 6/1991 | Ingaiz |
| 5,029,583 A | 7/1991 | Meserol et al. |
| 5,035,704 A | 7/1991 | Lambert et al. |
| 5,046,508 A | 9/1991 | Weissler |
| 5,049,487 A | 9/1991 | Phillips et al. |
| 5,054,499 A | 10/1991 | Swierczek |
| 5,066,859 A | 11/1991 | Kariar et al. |
| 5,068,181 A | 11/1991 | Driscoll |
| 5,070,886 A | 12/1991 | Mitchen et al. |
| 5,079,421 A | 1/1992 | Knudson et al. |
| 5,096,669 A | 3/1992 | Lauks et al. |
| 5,104,813 A | 4/1992 | Besemer et al. |
| 5,108,926 A | 4/1992 | Kiebe |
| 5,115,133 A | 5/1992 | Knudson |
| 5,146,091 A | 9/1992 | Knudson |
| 5,165,419 A | 11/1992 | Sarstedt |
| 5,179,005 A | 1/1993 | Phillips et al. |
| 5,179,951 A | 1/1993 | Knudson |
| 5,201,324 A | 4/1993 | Swierczek |
| 5,208,163 A | 5/1993 | Charlton et al. |
| 5,230,866 A | 7/1993 | Shartle et al. |
| 5,231,993 A | 8/1993 | Haber et al. |
| 5,242,606 A | 9/1993 | Braynin et al. |
| 5,252,044 A | 10/1993 | Raines et al. |
| 5,266,179 A | 11/1993 | Nankai et al. |
| 5,302,093 A | 4/1994 | Owens et al. |
| 5,304,468 A | 4/1994 | Phillips et al. |
| 5,309,176 A | 5/1994 | Faes et al. |
| 5,320,607 A | 6/1994 | Ishibashi |
| 5,338,688 A | 8/1994 | Deeg et al. |
| 5,368,047 A | 11/1994 | Suzuki et al. |
| 5,378,638 A | 1/1995 | Deeg et al. |
| 5,426,032 A | 6/1995 | Phillips et al. |
| 5,437,841 A | 8/1995 | Balmer |
| 5,453,360 A | 9/1995 | Yu |
| 5,458,140 A | 10/1995 | Eppstein et al. |
| 5,470,757 A | 11/1995 | Gagnon et al. |
| 5,472,603 A | 12/1995 | Schembri |
| 5,504,011 A | 4/1996 | Gavin et al. |
| 5,508,521 A | 4/1996 | Kraft et al. |
| 5,509,394 A | 4/1996 | Hitomi et al. |
| 5,563,031 A | 10/1996 | Yu |
| 5,563,042 A | 10/1996 | Phillips et al. |
| 5,575,632 A * | 11/1996 | Morris et al. .............. 417/477.2 |
| 5,582,184 A | 12/1996 | Erickson et al. |
| 5,591,403 A | 1/1997 | Gavin et al. |
| 5,627,041 A | 5/1997 | Shartle |
| 5,628,961 A | 5/1997 | Davis et al. |
| 5,638,828 A | 6/1997 | Lauks et al. |
| 5,674,699 A | 10/1997 | Saunders et al. |
| 5,677,195 A | 10/1997 | Winkler et al. |
| 5,682,233 A | 10/1997 | Brinda |
| 5,700,695 A | 12/1997 | Yassinzadeh et al. |
| 5,708,278 A | 1/1998 | Lowne |
| 5,728,352 A | 3/1998 | Poto et al. |
| 5,736,404 A | 4/1998 | Yassinzadeh et al. |
| 5,746,217 A | 5/1998 | Erickson et al. |
| 5,776,719 A | 7/1998 | Douglas et al. |
| 5,789,255 A | 8/1998 | Yu |
| 5,820,570 A | 10/1998 | Erickson et al. |
| 5,834,224 A | 11/1998 | Ruger et al. |
| 5,843,692 A | 12/1998 | Phillips et al. |
| 5,879,310 A | 3/1999 | Sopp et al. |
| 5,879,367 A | 3/1999 | Latterell et al. |
| 5,922,530 A | 7/1999 | Yu |
| 5,942,102 A | 8/1999 | Hodges et al. |
| 5,968,760 A | 10/1999 | Phillips et al. |
| 5,972,199 A | 10/1999 | Heller et al. |
| 6,001,307 A | 12/1999 | Naka et al. |
| 6,033,866 A | 3/2000 | Guo et al. |
| 6,066,504 A | 5/2000 | Jina |
| 6,083,174 A | 7/2000 | Brehmeier-Flick et al. |
| 6,084,660 A | 7/2000 | Shartle |
| 6,103,196 A | 8/2000 | Yassinzadeh et al. |
| 6,152,889 A | 11/2000 | Sopp et al. |
| 6,180,062 B1 | 1/2001 | Naka et al. |
| 6,193,873 B1 | 2/2001 | Ohara et al. |
| 6,206,841 B1 * | 3/2001 | Cunningham et al. ........ 600/584 |
| 6,261,519 B1 | 7/2001 | Harding et al. |
| 6,312,888 B1 | 11/2001 | Wong et al. |
| 6,335,203 B1 | 1/2002 | Patel et al. |
| 6,362,890 B1 | 3/2002 | Petrich et al. |
| 6,444,115 B1 | 9/2002 | Hodges et al. |
| 6,475,360 B1 | 11/2002 | Hodges et al. |
| 6,475,372 B1 | 11/2002 | Ohara et al. |
| 6,488,827 B1 | 12/2002 | Shartle |
| 6,521,110 B1 | 2/2003 | Hodges et al. |
| 6,521,182 B1 | 2/2003 | Shartle et al. |
| 6,531,322 B1 | 3/2003 | Jurik et al. |
| 6,541,266 B2 | 4/2003 | Modzelewski et al. |
| 6,554,789 B1 * | 4/2003 | Brugger et al. .............. 604/6.11 |
| 6,620,310 B1 | 9/2003 | Ohara et al. |
| 6,652,814 B1 | 11/2003 | House et al. |
| 6,656,697 B1 | 12/2003 | Ouyang et al. |
| 6,706,159 B2 * | 3/2004 | Moerman et al. ........ 204/403.03 |
| 6,716,577 B1 | 4/2004 | Yu et al. |
| 6,743,597 B1 | 6/2004 | Guo et al. |
| 6,872,297 B2 * | 3/2005 | Mansouri et al. ............. 205/775 |
| 2002/0064480 A1 | 5/2002 | Shartle |
| 2002/0110486 A1 | 8/2002 | Shartle et al. |
| 2002/0114738 A1 | 8/2002 | Wyzgol et al. |
| 2002/0143437 A1 | 10/2002 | Handique et al. |
| 2002/0169411 A1* | 11/2002 | Sherman et al. ................. 604/48 |
| 2003/0023189 A1* | 1/2003 | Kuo ............................. 600/584 |
| 2003/0031594 A1 | 2/2003 | Shartle et al. |
| 2003/0044318 A1 | 3/2003 | Olson |
| 2003/0073931 A1 | 4/2003 | Boecker et al. |
| 2003/0083685 A1 | 5/2003 | Freeman et al. |
| 2003/0141473 A1 | 7/2003 | Pelrine et al. |
| 2003/0156984 A1 | 8/2003 | Lemke et al. |
| 2003/0212347 A1 | 11/2003 | Sohrab |
| 2003/0212379 A1* | 11/2003 | Bylund et al. ................. 604/504 |
| 2004/0096959 A1 | 5/2004 | Stiene et al. |
| 2004/0204662 A1* | 10/2004 | Perez et al. ................... 600/583 |

FOREIGN PATENT DOCUMENTS

| | | |
|---|---|---|
| EP | 0 160 768 A1 | 11/1985 |
| EP | 0 212 906 A2 | 4/1986 |
| EP | 0 199 484 A2 | 7/1986 |
| EP | 0 250 257 A1 | 6/1987 |
| EP | 0374115 A1 | 6/1990 |
| EP | 0453283 A1 | 10/1991 |
| EP | 0 582 226 A1 | 7/1993 |
| EP | 0803288 | 4/1997 |
| EP | 0 922 954 A2 | 6/1999 |
| EP | 0 974 840 A2 | 7/1999 |
| EP | 0 974 840 A | 1/2000 |
| EP | 1 069 427 A2 | 1/2001 |
| EP | 1 260 815 | 11/2002 |
| EP | 1260815 A | 11/2002 |
| EP | 1 279 436 A2 | 1/2003 |
| GB | 2 033 375 | 5/1980 |
| GB | 1526708 | 9/2003 |
| WO | WO 85/04089 | 9/1985 |
| WO | WO 88/00812 | 2/1988 |
| WO | WO 91/18548 | 12/1991 |
| WO | WO 93/22452 | 11/1993 |
| WO | WO 94/02850 | 2/1994 |
| WO | WO 95/10223 | 4/1995 |
| WO | WO 95/12117 | 5/1995 |
| WO | WO 97/18465 | 5/1997 |
| WO | WO 99/18426 | 4/1999 |

| | | |
|---|---|---|
| WO | WO 99/34957 | 7/1999 |
| WO | WO 99/49307 | 9/1999 |
| WO | WO 02/18785 | 3/2002 |
| WO | WO 02/49507 | 6/2002 |
| WO | WO 2004/045770 | 6/2004 |

OTHER PUBLICATIONS

Ash et al., "Subcutaneous capillary filtrate collector for measurement of blood glucose", ASAIO Journal, (1992), vol. 38, pp. M416-M420.

Arnold et al., "Determination of physiological levels of glucose in an aqueous matrix with digitally filtered fourier transform near-infrared spectra", Anal. Chem, pp. 1457-1465 (1990).

Brace et al., "Reevaluation of the needle method for measuring Interstitial fluid pressure", Am. J. Physiol., (1975), vol. 229, No. 3, pp. 603-607.

Bohn et al., "A micromachined silicon valve driven by a miniature bi-stable electro-magnetic actuator", Sensors and Actuators 80 (2000) 77-83.

DuPuy, et al., "Quantitative analysis of aqueous solutions by FTIR spectroscropy of dry extract", SPIE, (1991) vol. 1575, $8^{th}$ international conference of fourier transform spectroscopy, pp. 501-502.

European Search Report, dated Feb. 9, 2004, for European Appln. No. 01 961 740.6.

Fu et al., "An integrated microfabricated cell sorter", Anal. Chem. 2002, 74, 2451-2457.

Gelman Science brochure, pp. 60 (1993) showing Nylaflo, catalog P/N 32378.

Gilanyi, et al., "Ion concentrations in subcutaneous interstitial fluid: measured versus expected values", Am. J. Physiol. (1998), 255 (3 pt 2) pp. F513-F519.

Ginsberg, "An overview of minimally invasive technologies", Clinical chemistry, (1992), vol. 38, No. 9, pp. 1596-1600.

Gimbal definition from English Oxford Dictionary online: http://dictionary.oed.com/cgi/entry/00094657?signle=1&query_type=word&queryword=gimbal&edition-2e&first=1&max_to_show=10.

"Glucose sensors", and "Like an injection" sections on p. 26 of Diabetes Forecast, May 1993.

Grover, et al. "Monolithic membrane valves and diaphragm pumps for practical large-scale integration into glass microfluidic devices," Elsevier, Sensors and Actuators B 89 (2003) 315-323.

Handique, et al. "On-chip thermopneumatic pressure for discrete drop pumping," Anal. Chem. 2001, 73, 1831-1838.

Handique, et al. "Nanoliter liquid metering in microchannels using hydrophobic patterns," Anal. Chem. 2000, 72, 4100-4109.

Janle-Swain et al., "Use of capillary filtrate collector for monitoring glucose in diabetes", Trans. Am. Artif. Intern. Organs, (1987), vol. XXXIII, pp. 336-340.

Kayashima et al., "New noninvasive transcutaneous approach to blood glucose monitoring: successful glucose monitoring on human 75 g OGTT with novel sampling chamber", IEEE Transactions on biomedical engineering, (1991) vol. 38, No. 8, pp. 752-757.

Kayashima et al., "Suction effusion fluid from skin and constituent analysis: New candidate for interstitial fluid", Am J Physiol (United States) Nov. 1992, 263 (5PT 2) p. H1623-7/.

Khstala, U., "Suction blister device for separation of viable epidermis from dermis", Journal of Investigative Dermatology, (1968), vol. 50, No. 2, pp. 120-137.

Korthius et al., "Method for sampling interstitial fluid", from book entitled Microcirculatory Technology, edited by D.H. Baker et al., Academic Press, Chapter 21, pp. 326-327 (1986).

Madou et al., "Design and fabrication of polymer microfluidic platforms for biomedical applications,"Bio. Microdevices, 3:3, 2534-2538, 2001.

Mendelson, et al., "Blood glucose measurement by multiple attenuated total reflection and infrared absorption spectroscopy", IEEE, transactions on biomedical engineering, (1990) vol. 37, No. 5, pp. 458-465.

Moatti-Sirat et al., "Towards continuous glucose monitoring: in vivo evaluation on miniaturized glucose sensor implanted for several days in rat subcutaneous tissue", Diabetologia (1992), vol. 35, pp. 224-230.

Moroney et al., "A passive fluid valve element for a high-density chemical synthesis machine,"Technical Proceedings of the 1999 International Conference on Modeling and Simulation of Microsystems, Chapter 15: Computational Methods for Microfluidics, pp. 526-529.

Peterson L., et al., "Microdialysis of the interstitial water space in human skin in vivo: quantitative measurement of cutaneous glucose concentrations", J Invest Dermatol. (1992), vol. 99, No. 3, pp. 357-360.

Stimpson, et al., "Parallel production of oligoncleotide arrays using membranes and reagent jet printing", Biotechniques, vol. 25, No. 5, Nov. 1998, pp. 886-890.

Turner, et al., "Diabetes mellitus: biosensors for research and management", Biosensors (1985), vol. 1, pp. 85-115.

Wilig et al., "Evaluation of methodologies for measurement of interstitial fluid pressure (Pi): physiological implications of recent Pi data", Crit Rev Biomed Eng (United States) 1990, vol. 18, No. 1, pp. 27-54.

Wolfson, Jr., et al., "Glucose concentration at possible sensor tissue implant sites", Diabetes, (1982), vol. 5, No. 3, pp. 162-165.

Zeng, et al. "Fluidic capacitance model of capillary-driven stop valves," ASME, proc. 2000.

U.S. Appl. No. 60/558,375, filed Mar. 31, 2004, Bohm.

U.S. Appl. No. 60/558,390, filed Mar. 31, 2004, Bohm.

European Communication, Munich, Germany, Jul. 6, 2007, re European Application 5253672.9.

Japanese Patent Application No. 2005-190289, Notice of Reasons for Refusal, dated Sep. 28, 2010, 5 pages, Japanese Patent Office, Japan.

* cited by examiner

FLUID HANDLING DEVICES

BACKGROUND OF THE INVENTION

A variety of medical diagnostic procedures involve tests on biological fluids, such as blood, urine, or saliva, and are based on a change in a physical characteristic of such a fluid or an element of the fluid, such as interstitial fluid, blood, etc.

A variety of devices have been developed for performing tests on fluids. In many such devices, fluid is introduced into the device at one location but analyzed at another. In such devices, movement of the introduced fluid from the introduction location to the measurement location is necessary. As such, these devices require a reliable way in which to move fluid from an introduction site to a measurement site easily and without adversely affecting the fluid.

A variety of different design configurations have been developed to provide for this fluid movement. One type of device relies on capillary action to move fluid through the device, where the fluid paths through the device are dimensioned to provide for this capillary action. Other designs include those intended for use with gravity, those intended for use with injection of the sample under pressure, and the like. However, moving fluid using these types of device may not be completely reliable. For example, gravity may not provide enough force to efficiently move a fluid in a flow path or flow may not be controllable.

As the interest in devices for testing an analyte continues, a need for devices that are capable of reliably moving fluid between different areas of the device remains.

SUMMARY OF THE INVENTION

Fluid handling devices for determining the concentration of an analyte in a fluid are provided. Embodiments of the subject fluid handling devices include a skin piercing element, at least one analyte sensing chamber and a pumping chamber having a deflectable membrane, wherein the pumping chamber is capable of transporting fluid from the skin piercing element to a sensing chamber upon deflection of the deflectable membrane. Also provided are novel kits that include the subject devices.

DETAILED DESCRIPTION OF THE INVENTION

Fluid handling devices for determining the concentration of an analyte in a fluid are provided. Embodiments of the subject fluid handling devices include a skin piercing element, at least one analyte sensing chamber and a pumping chamber having a deflectable membrane, wherein the pumping chamber is capable of transporting fluid from the skin piercing element to a sensing chamber upon deflection of the deflectable membrane. Also provided are novel kits that include the subject devices.

Before the present invention is described, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "an", and "the" include plural referents unless the context clearly dictates otherwise.

When two or more items (for example, elements or processes) are referenced by an alternative "or", this indicates that either could be present separately or any combination of them could be present together except where the presence of one necessarily excludes the other or others.

It will also be appreciated that throughout the present application, that words such as "top", "bottom" "front", "back", "upper", and "lower" and analogous terms are used in a relative sense only.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention.

The figures shown herein are not necessarily drawn to scale, with some components and features being exaggerated for clarity.

Devices

As summarized above, embodiments of the subject invention include fluid handling devices, where in many embodiments the fluid handling devices are employed for determining the concentration of an analyte in a fluid. Embodiments of the fluid handling devices of the subject invention provide for controlled delivery of physiological fluid extracted from a subject, e.g., such as interstitial fluid and the like, to analyte (e.g., glucose) monitoring sensors located within the device, as described below.

Embodiments of the subject invention include a pumping chamber that is capable of transporting fluid from a first region of the device to a second region of the device, wherein in many embodiments this pumping chamber may be actuated automatically, e.g., by an actuator under the control of a processor. The pumping chamber may be employed to controllably start and stop the flow of fluid in a flow pathway, e.g., repeatedly.

As will be described in greater detail below, embodiments include devices that are in fluid communication with a skin piercing element, e.g., a skin piercing element may be temporarily (removably) or permanently affixed to the device. In such embodiments, the pumping chamber is configured to transport fluid from the skin piercing element to a sensing chamber in the device upon actuation of the pumping chamber.

The subject fluid handling devices include fluid processing features (analyte sensing chambers) for measuring and/or analyzing or otherwise evaluating one or more aspects of a fluid introduced to the device. The sensing chamber of the subject fluid handling devices may have an electrochemical, photometric or colorimetric configuration by which to perform a measurement on a sampled fluid.

The subject fluid handling devices may be used to process a variety of organic and inorganic fluids as will be apparent to those of skill in the art. It is to be understood that the subject invention is not limited to any particular liquid or type of fluid. The fluids may be naturally occurring or synthetic, and may be pre-processed or otherwise manipulated prior to use with the subject devices. That is, a wide variety of fluids may be processed (e.g., measured, detected, separated, analyze, and the like) according to the subject invention, where fluids include, but are not limited to, whole blood, interstitial liquid, plasma, buffer or buffer-containing sample, etc. For example, a sample of whole blood, interstitial liquid, plasma, cell suspensions, protein solutions, serum, urine, tears, water, buffer or buffer-containing liquid, and the like, may be contacted with a subject device and processes, e.g., for analyte determination. In many embodiments, the fluid is a bodily fluid such as blood or interstitial fluid.

The size of a given fluid handling device may vary widely depending on the particular analytical protocol performed and, as such, may include small scale or miniaturized devices known in the art. In certain embodiments, the devices are dimensioned to be comfortably worn or otherwise retained by a user, as described below. Embodiments of the subject devices may be used with submicroliter, nanoliter and even picoliter amounts of fluid. Such fluid handling devices may be characterized as microfluidic devices such that they include one or more pathways or channels of extremely small or microfluidic dimensions. By "microfluidic" is meant that the device includes one or more liquid pathways or channels, conduits, or reservoirs that has at least one dimension, e.g., depth, width, length, etc., that ranges from about 5 microns to about 2500 microns. In certain embodiments, all of the fluid pathways may be so dimensioned. A fluid pathway of the subject invention may have a depth that ranges from about 5 microns to about 500 microns, e.g., from about 25 microns to about 500 microns, and/or a width that may range from about 25 microns to about 500 microns, and/or a length that may range from about 1,000 microns to about 5,000 microns. Exemplary microfluidic and other devices that may be adapted for use with the subject invention are described, e.g., in international publication no. WO 02/49507, as well as U.S. application Ser. No. 10/143,253, which was filed on May 9, 2002, entitled "Devices and Methods for Accessing and Analyzing Physiological Fluid; U.S. application Ser. No. 60/558,375, which was filed on Mar. 31, 2004, entitled "Pneumatic Liquid Handling Circuit"; and U.S. application Ser. No. 60/558,390, which was filed Mar. 31, 2004, entitled "Triggerable Passive Valves," the disclosures of which are herein incorporated by reference.

Figure 1:
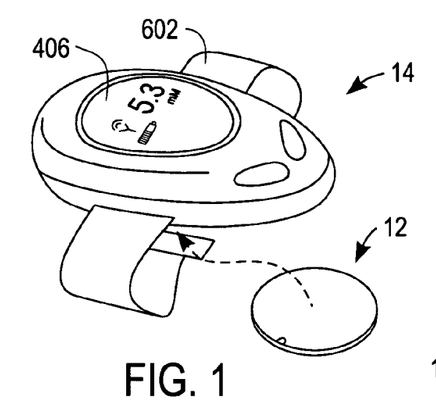
FIG. 1 illustrates a fluid handling device and a housing in the form of a local controller module according to an exemplary embodiment of the present invention.

Turning now to the figures, FIG. 1 illustrates an exemplary embodiment of a fluid handling device 12 and housing structure 14, within which device 12 may be operatively loaded, and which in this case is in the form of local controller module 14. Local module 14 controls certain functions of device 12 and may be a microprocessor. As illustrated in FIG. 1, fluid handling device 12 has yet to be received by (e.g., inserted partially or completely into) local controller module 14.

During use, fluid handling device 12 may be received in local controller module 14. In such embodiments, device 12 may be coupled to the local controller module 14 to enable electrical communication between the local controller module and a device received thereby. Accordingly, embodiments include fluid handling device 12 operatively coupled to (e.g., located within and controlled by) local controller module 14. When fluid handling device 12 is coupled to local controller module 14, local controller module is in electrical and mechanical contact with fluid handling device 12. In this manner, analyte measurement control may be provided by module 14 and/or module 14 may receive measurement data from device 12 such as data related to the concentration determination of an analyte in a fluid contacted with device 12. Connectors or contacts are provided to operatively couple the devices with a local controller module whereby the local controller module provides the requisite signals to the devices to perform the assay measurement and includes a componentry for determining the value of such measurement. As noted above, local module 14 may control the functions of device 12, e.g., actuation of a pumping chamber of the device as will be described, and other functions of device 12 described herein. Local controller module 14 may be capable of data storage and transmitting and receiving data from another source such as a remote source.

Local controller module 14 is programmable such that an assay protocol performed at a sensor chamber of the device and the timing thereof may be customized according to software algorithms. Such algorithms may provide for the "continuous" monitoring of concentration of an analyte in a user, i.e., for automatically measuring the concentration of an analyte in a user according to a predetermined scheduled, e.g., at two or more points over a given time period or even continuously over a period of about 24 hours, 48 hours, etc. For example, embodiments of the subject devices may be configured to remain in intimate contact with a user and continuously or periodically obtain sample from the user and monitor one or more analyte concentrations over a given period of time, where in many embodiments sampling and analyte determination are performed automatically according to an algorithm of the device. Embodiments of the subject invention may also provide for the user to implement an assay "on demand," thereby overriding the continuous monitoring protocol. Such analyte concentration measurements may be stored by the microprocessor of module 14 or other memory storage element (such as communicated to a remote location, e.g., to remote controller module 16 described below) for immediate or later retrieval by the user or a physician.

In combination, fluid handling device 12 and local controller module 14 may be user-retainable, e.g., they may be worn by a user, such as on the user's arm or the like, e.g., as shown in the figures. In this particular embodiment, module 14 includes straps 602 for attachment to the arm of a user. Continued use by a subject for minutes such as several minutes or more, e.g., an hour or multiple hours, a day or multiple days or more, etc., is contemplated with the subject invention. Use for an extended period of time is contemplated. In certain instances, a device 12/controller 14 system may be worn or retained by a subject for up to about 24 hours or longer. Module 14 may incorporate other forms of user-retainable elements such as patches, plates, bandages, strips, wraps, sleeves, bracelets, suction cups, and the like. In this manner, embodiments of the subject devices are suited for sustained or continued use by a user. As the subject devices includes on or more analyte sensors, the present invention integrates sensor formats that are amenable to prolonged retention by a patient. Maintaining a subject device in close anatomic association with a user for an extended period through the use of an easily-retainable support allows for constant or periodic monitoring (e.g., analyte monitoring such a glucose monitoring) by a user, physician or other care provider. In many embodiments, this monitoring is accomplished automatically.

Accordingly, local controller module 14 may have a skin-facing portion and/or surface which appositions fluid handling device 12 loaded within and fluid handling device 12 may have a skin piercing element affixed thereto for continuous indwelling of the skin piercing element to a section of the user's skin while module 14/device 12 are maintained at the site of the user. Local controller module 14 may be configured so as to be maintained against the skin for extended periods, as noted above. To this end, local controller module 14 may have a "watchband", "legband", or "armband" configuration in certain embodiments to be worn by a user, e.g., worn on a limbic region, e.g., a wrist or forearm, of the user. Housing 14 may have a configuration, such as a substantially planar configuration, for adhesive contact with a suitable location, e.g., arm, torso, thigh, hip, etc., on the user's body.

Local controller module 14 may include first data display 406 which may provide audio and/or visual indicators to a user.

Figure 2:
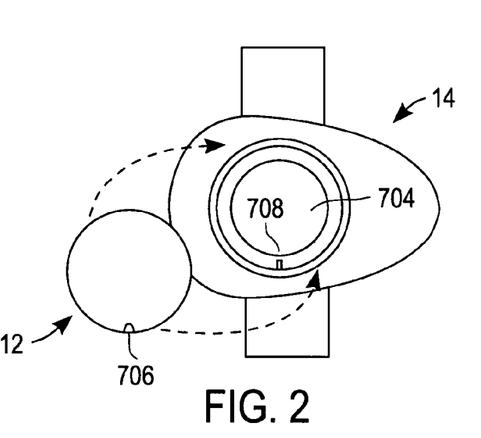
FIG. 2 illustrates the fluid handling device and local controller module of FIG. 1 from another perspective.

FIG. 2 illustrates fluid handling device 12 prior to insertion into local controller module 14. Local controller module 14 may be provided with insertion cavity 704, and may be configured to accept fluid handling device 12. Local controller module 14 may be in electrical communication with fluid handling device 12 by way of contact pad 706 on fluid handling device 12 and contact pin 708 located within insertion cavity 704. As noted above, this electrical communication may provide for local module control of aspects of device 12, e.g., aspects of analyte concentration determination such as timing thereof (e.g., timing of pump actuation, assay timing, etc.). For example, local module 14 may control aspects of fluid transport of fluid handling device 12 such as the timing of the stop and start of fluid transport from the user through the skin piercing element and to an analyte sensor of the device.

Figure 3:
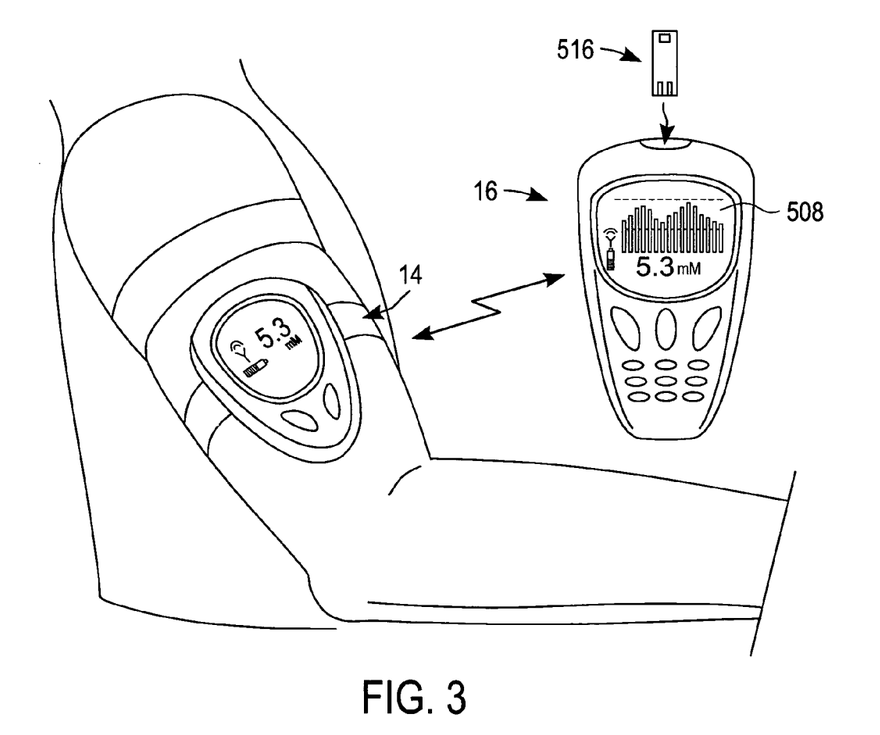
FIG. 3 illustrates the fluid handling device and local controller module of FIG. 1 retained in a fixed position on an arm of a user. Also shown is an exemplary embodiment of a remote controller module according to the present invention.

FIG. 3 illustrates attachment of fluid handling device 12 and local controller module 14 onto the arm of a user. FIG. 3 also illustrates optional remote controller module 16 located within communication range of local controller module 14. Either a physical connection or remote/telemetry type connection may be employed to provide communication between remote controller module 16 and local controller module 14. Communication between local controller module 14 and remote controller module 16 may be by way of radio frequency (RF), or other wireless means. For example, RF signals sent and received by first and second telemetry units, respectively may be employed. An exemplary system which may be adapted for use in the subject invention is disclosed in U.S. Pat. No. 6,083,174 to Brehmeier-Flick, the disclosure of which is herein incorporated by reference. Other telemetry units and applications thereof well known in the art are also applicable to the present invention. Regardless, transmission of data to other diagnostic and/or data storage device(s) such as to remote controller module 16 from local controller module 14 may be carried out in any suitable fashion, e.g., in burst or continuous fashion. Telemetry for use in the home is contemplated. In the case of a hospitalized patient, telemetry of data to a central Intensive Care Unit (ICU) station provides another example of use.

Remote controller module 16 may include a second data display 508. Display 508 may be an audio and/to visual display for displaying results, e.g., analyte measurement results, to a user. In certain embodiments, remote controller module 16 may be configured to receive a test strip 516 for determining analyte concentration by way of a received test strip. In this manner, remote controller module 16 may be used with local controller module 16 and device 12 to determine analyte concentration of a fluid applied to device 12 and may be capable of analyte determination of a fluid applied to a test strip received by module 16.

As illustrated in FIGS. 1, 2, and 3, and as noted above, fluid handling device 12 may be mounted on an arm, or other suitable location of a user, and may be used to monitor an analyte in a bodily fluid such as blood glucose in interstitial fluid. For example, a skin piercing element as noted above may be incorporated into device 12 for piercing, cutting or lancing the skin and, in many embodiments, also includes a fluid collection channel or transfer pathway for transferring the sampled physiological fluid such as for example interstitial fluid within the skin to fluid handling device 12 with which it is operatively associated. Skin piercing elements and methods of using skin piercing elements which may be adaptable for use with the subject invention, are described for example in U.S. Ser. No. 10/143,253, the disclosure of which is herein incorporated by reference. The skin piercing element may be any suitable element capable of accessing bodily fluid, e.g., a needle such as small gauge needle, e.g., about 25 to about 30 gauge needle. In certain embodiments, the insertion depth of a needle may range from about 1.5 mm to about 3 mm. In certain embodiments, a skin piercing element may be retractable inside device 12 and may be moved from a first retractable position to a second fluid accessing position outside the device to contact a user. This may be done repeatedly over a given time period to provide periodic analyte monitoring over a period of time. Actuation of a skin piercing element from a retracted position to a skin-piercing position may be manual or automatic, e.g., may be under the control of local module 14 or remote module 16. For example, advancement of a skin-piercing element to a position for collecting physiological fluid from a user may be performed manually by the user or driven by a motor controlled by local controller module 14. Such advancement and skin-penetration may be done automatically according to a preprogrammed scheduled or at the will of the user in certain embodiments.

In certain embodiments, a skin piercing element is provided to a user already affixed to device 14 or may be provided separately and a user may select a skin piercing element when needed and affix it to fluid handling device 12. For example, a skin piercing element may be affixed (e.g., at manufacture or by a user prior to use) about inlet chamber 140.

In certain embodiments, a plurality of skin piercing elements may be incorporated into a cartridge associated with fluid handling device 12. Such a cartridge may include a plurality of skin piercing elements. Device 12 (and/or local controller module 14) may further provide componentry for operatively moving, e.g., advancing and reversing, a cartridge relative to an aperture of fluid handling device 12 (and/or local controller module 14) for exposing and concealing an individual skin-piercing element through the aperture to an access site on the user's skin. Alternately, at least a portion of the apertured device may be moveable to expose and unexposed an individual skin-piercing element for fluid sampling.

The movement of a skin-piercing element relative to a cartridge, if employed, may be accomplished passively such as by components fixed within the local controller module relative to the cartridge for advancing or deflecting a skin-piercing element through a device aperture towards an access site on the user, penetrating the access site with the skin-piercing element and then withdrawing or retracting the skin piercing element from the access site. Such components include, but are not limited to, ramp structures and clip mechanisms. As noted above, the timing of skin piercing may be controlled automatically for example by local controller 14 and/or remote controller 16 such that fluid sampling and analyte determination may be automated. In this manner, such may be accomplished passively with respect to a user in that the user need not actively initiate skin piercing and/or physiological fluid flow and/or analyte measuring. This may be particular convenient for in instances where multiple skin piercing and/or physiological fluid flow and/or analyte measuring cycles need to be performed over a given period, e.g., over about 24 hours, for example for monitoring glucose levels over this period.

In those embodiments in which a skin piercing element (or plurality of skin-piercing elements) translate along with a cartridge device operatively associated (e.g., partially or completely integrated) with device 12 and/or local controller module 14, in some embodiments each skin piercing element may be operatively attached to the cartridge device so as to be movable relative to the cartridge device so as to optimize the angle by which the skin is to be pierced by the skin-piercing means, thereby reducing pain to the patient and trauma to the skin, e.g., as described in the above-mentioned U.S. patent application Ser. No. 10/143,253.

Figure 4:
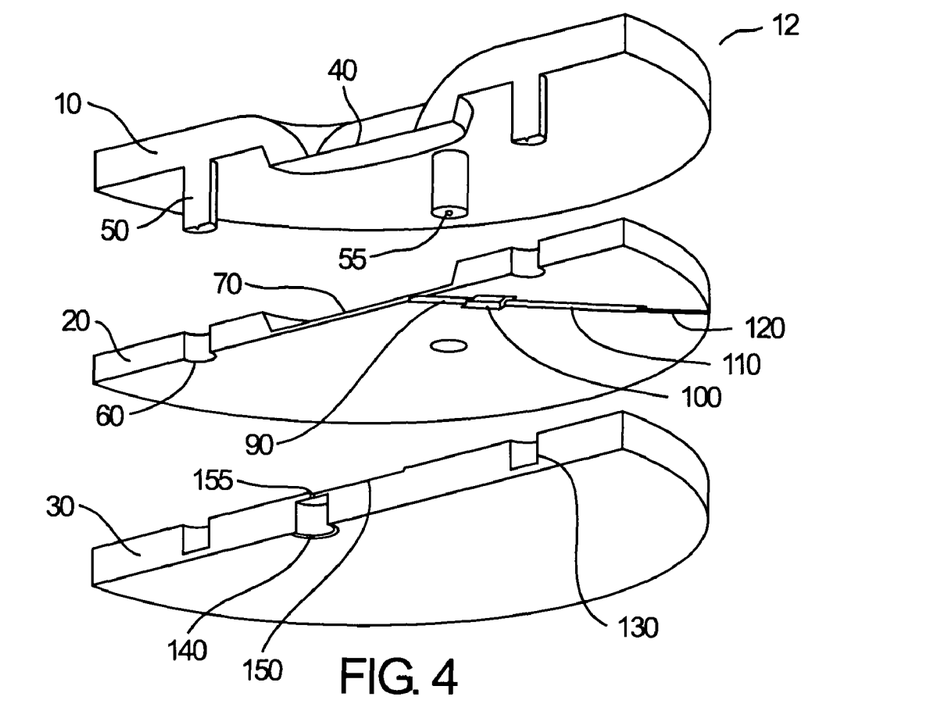
FIG. 4 is an exploded view of the fluid handling device of FIG. 1.

FIG. 4 is an exploded view of fluid handling device 12. In this particular embodiment, fluid handling device 12 includes three parts: pressure disk 10, elastomeric disk 20, and sensor disk 30. Pressure disk 10 and sensor disk 30 may be rigid, while elastomeric disk 20 may be flexible. "Flexible" with reference to a substrate or broadly references that the substrate may be bent without breaking. The substrate may be so bent and straightened repeatedly in either direction at least 100 times without failure (for example, cracking) or plastic deformation. This bending must be within the elastic limits of the material. The foregoing test for flexibility may be performed at a temperature of about 20° C. "Rigid" broadly refers to a substrate which is not flexible, and is constructed such that it cannot be bent along any direction more than about 60 degrees (and often not more than 40, 20, 10, or 5 degrees) without breaking.

As shown, pressure disk 10 includes access slot 40, assembly bosses 50, and energy directors 55. Elastomeric disk 20 includes clearance holes 60, deflectable pump membrane 70, inlet channel 90, sensor chamber 100, waste channel 110, and vent 120. Sensor disk 30 includes pumping chamber 150, inlet chamber 140, and assembly recesses 130. Inlet chamber 140 may be in contact with a skin piercing element as described above (not shown) that may be inserted into the tissue of the user, allowing extraction of physiological fluid such as interstitial fluid from the user. In certain embodiments, a skin piercing is in direct or indirect communication with inlet chamber, e.g., inlet chamber may include a skin piercing element, e.g., may be a part of the inlet chamber.

Pressure disk 10 and sensor disk 30 may be fabricated using any suitable technique. For example, pressure disk 10 and/or sensor disk 30 may be injection molded using thermoplastic polymers. Suitable polymers include, but are not limited to, acrylic, stryrene, polycarbonate, ABS, and polyolefins. Blends of these polymers may also be used. Certain embodiments may employ ultrasonic welding in the assembly of pressure disk 10 to sensor disk 30. In such instances, polymers may be selected that are amorphous in structure, as opposed to crystalline, as amorphous polymers are more suitable for ultrasonic welding. One of skill in the art will appreciate that injection molding is capable of providing product of exacting detail, and may be employed to easily form the features of pressure disk 10 and sensor disk 30. Pressure disk 10 and sensor disk 30 may be used as molded, or they may be subjected to post treatment to render their surfaces more hydrophilic. Post processes include, but are not limited to, exposing the parts to reactive gas plasma or corona, or coating the surfaces with hydrophilic materials.

Elastomeric disk 20 may be fabricated using any suitable technique, e.g., elastomeric disk 20 may be molded, using injection molding or reaction injection molding. Elastomeric disk 20 may also be cast. In any of these methods, the ability to replicate fine detail is necessary. Suitable materials for construction of elastomeric disk 20 include a wide variety of natural and synthetic rubbers, including, but not limited to, silicones, polyurethanes, EPDM, and various polymer blends. In selecting the material, biocompatibility and flexibility are important attributes to consider. If necessary, post treatment may be used to render the surfaces more hydrophilic. If the parts are used as molded, tracks and channels formed in elastomeric disk 20 and sealed with surfaces on pressure disk 10 and sensor disk 30 are less likely to leak, since the parts may be hydrophobic when used as molded.

When pressure disk 10, elastomeric disk 20, and sensor disk 30 are assembled, access slot 40 in pressure disk 10 allows an actuator to make contact with pump membrane 70 in elastomeric disk 20. An actuator may be provided as part of local controller 14. Actuation may be performed manually by the user or may be performed automatically, e.g., driven by a motor or the like controlled by the local controller module 14. Other manners and componentry that enable an actuator to make contact with pump membrane 70 may also be employed. The actuator may make contact on one end of pump membrane 70, then slide towards the other end, in this way providing a peristaltic pumping motion. Any suitable actuator or technique for actuation may be employed.

For example, the pumping chamber 150 (which may be dish shaped in certain embodiments) has a fixed volume, which may be in the range of nanoliters. Upstream from pumping chamber 150 is connecting channel 155 and downstream is outlet channel 90 which is located in the elastomeric disk 20. In certain embodiments, actuation may be accomplished as now described with reference to FIGS. 8 and 9. As now described in greater detail, a method of handling a fluid may include collecting fluid in pumping chamber 150, e.g., to introduce fresh or new fluid to chamber 150, optionally pinching pumping chamber 150 to stop the flow of the fluid, collapsing a predetermined length of pumping chamber 150 to dispense a fixed volume of fluid towards a sensor, performing a measurement on the fluid present at the sensor, de-collapse (i.e., stop the collapse of) the predetermined length of pumping chamber 150 and de-pinch (i.e., stop the pinching of) pumping chamber 150.

Figure 8:
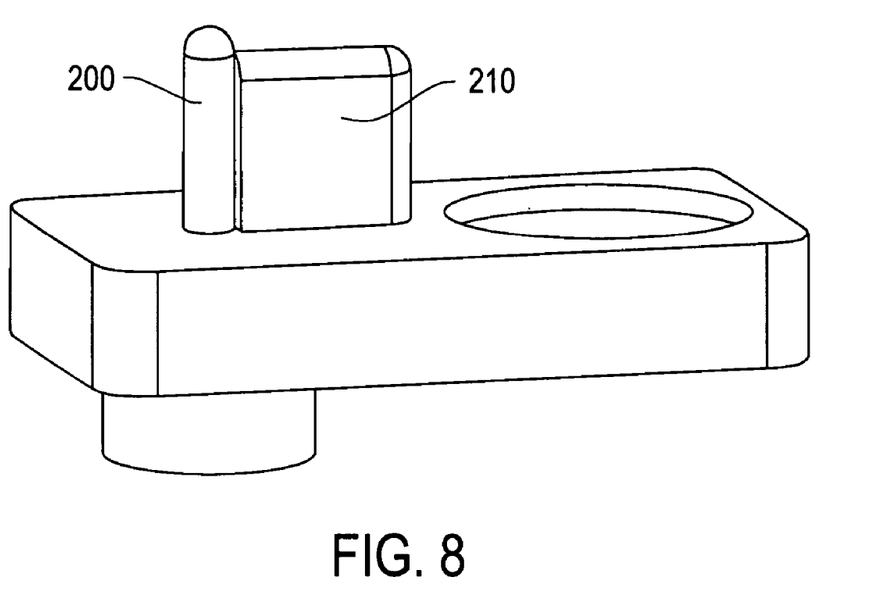
FIG. 8 is an exemplary embodiment of an actuator according to the subject invention.
Figure 9:
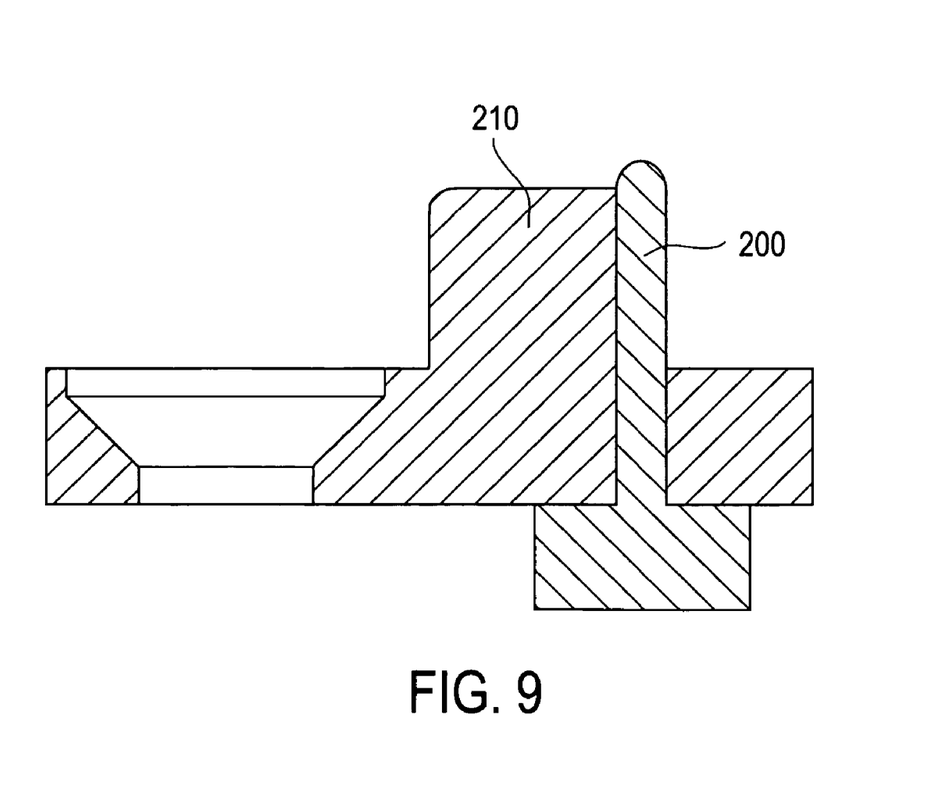
FIG. 9 is a cross-sectional view of the actuator of FIG. 8.

In this manner, a two-step activation may be achieved with a single movement. By deforming pumping membrane 70 through a spring (not shown) loaded pinching pin 200 or the like, connecting channel 155 will be closed with the first movement. This will stop the flow of fluid from the inlet. With further movement of the pinching body 210, pumping membrane 70 will be squeezed into pumping chamber 150 and the fluid will be pumped along the outlet channel 90 and along the rest of the fluidic structure. In this manner, the pump volume of fresh fluid refreshes the sensor chamber 100 more than once.

By controlling the speed of pinching body 210 movement, it is possible to make an analyte measurement during controlled flow, or by stopping the actuator after it has completely deformed the pumping membrane 70 into the pumping channel 90. It is also possible to make an analyte measurement under stopped flow conditions.

By removing the pinching body 210, the fluid may be drawn back from outlet channel 90 into pumping chamber 150, at which point there is no mixing between "used" and "fresh" fluid, as connecting channel 155 is still closed by the deformation of the pumping membrane 70 by pinching pin 200. With further movement, pinching pin 200 may be removed, thereby opening connecting channel 155 and letting fresh fluid flow into pumping chamber 150.

In certain embodiments, the dispensed volume of fluid (in the pinch-collapse mode) is at least as great as the combined volume of the connecting channel and the sensor volume. This ensures that the sensor is contacted with fresh fluid for analyte sensing. For example, the dispensed volume of fluid (in the pinch-collapse mode) may be about 1.5 times or more as large as the combined volume of the connecting channel and the sensor volume, e.g., about 3 times as large, e.g., about 5 times as large, in certain embodiments.

The amount of pressure required to deflect membrane 70 may vary. In certain embodiments, the amount of pressure may range from about 0.1 N to about 10 N.

Assembly bosses 50 on pressure disk 10 include energy directors 55 that are mateable with assembly recesses 130. Energy directors may be any suitable shape such as for example conical in shape, and are used to focus pressure and ultrasonic energy. In this way, energy directors 55 and assembly recesses 130 are fused. When assembled, pressure disk 10 and sensor disk 30 squeeze elastomeric disk 20, sealing the channels and chambers that are formed.

Elastomeric disk 20 includes clearance holes 60, that allow assembly bosses 50 to reach assembly recesses 130. Pump membrane 70 forms the top of pumping chamber 150, thus forming a deformable channel. An actuator may be introduced by way of access slot 40, deforming pump membrane 70 and forcing fluid out of pumping chamber 150. When assembled, elastomeric disk 20 and sensor disk 30 form inlet channel 90, sensor chamber 100, waste channel 110, and vent 120. Pumping chamber 150 is connected to inlet channel 90, and when actuated, causes fluid to flow from pumping chamber 150 to inlet channel 90, sensor chamber 100, and waste channel 110, or other connected conduits. Air that is displaced flows out of the device by way of vent 120, preventing a build up of back pressure.

Sensor chamber 100 (Also referred to as a reaction chamber) provides for accumulation of sample from pumping chamber 150, and overlays a sensor located on sensor disk 30, i.e., an electrode positioned on sensor disk 30 (e.g., printed thereon) In this particular embodiment, only one sensor chamber is shown. However a plurality of sensor chambers may be employed, e.g., for serial and/or parallel processing of a sample in a plurality of sensor chambers. In this manner, using the pumping chamber of the device, flow of fluid may be stopped, processed at a sensor chamber, and flow initiated again to transport the fluid to another region where the fluid may be stopped, processed at another reaction chamber, and flow initiated again to transport the fluid to another region, etc., all by way of pumping chamber actuation and de-actuation.

Sensor chamber 100 produces a signal in response to the presence, and concentration of, analyte in physiological fluid present in the chamber. The sensor chamber may have a volume in the range from about 25 nL to about 2000 nL. Sensor chamber 100 may be of any suitable configuration and include any suitable componentry and/or chemicals for generating a signal in response to the presence of analyte in fluid present in the chamber. While in the broadest sense a signal that is indicative of the presence of analyte may be provided, in many embodiments a signal that is proportional to the amount of analyte in the physiological fluid may be provided.

When assembled, inlet channel 90 is formed between elastomeric disk 20 and sensor disk 30. Inlet channel 90 provides a conduit between pumping chamber 150 and sensor chamber 100. Waste channel 110 is formed down stream of sensor chamber 100, and receives sample after it has passed through sensor chamber 100. Waste channel 110 provides space for accumulation of spent sample, such as sample where measurements have been made or where measurements are not desired. In certain embodiments, fluid may be passed from waste channel 110 to another analyte sensor, e.g., by actuating a pumping chamber, which pumping chamber may be the same or different from one that caused fluid to flow into the waste channel. Vent 120 is downstream of waste channel 110, and provides for escape of displaced air to atmosphere. Vent 120 is shown as exiting the disk on its perimeter, but may also exit the assembly through its top or bottom surfaces.

Sensor disk 30 includes assembly recesses 130 that receive assembly bosses 50 when assembled. Assembly recesses 130 are sized to allow adequate clearance for assembly bosses 50, and include a flat surface that allows contact with energy directors 55. Inlet connector or chamber 140 is provided, and is connected to a skin piercing element such as a sampling needle (not shown). In certain embodiments, care should be taken to minimize accumulation of liquid in connector 140. Inlet chamber 140 is upstream of pumping chamber 150 which provides space for accumulation of sample from the skin piercing element Accumulation of liquid takes place within chamber 150 as old liquid is replaced with new liquid, as the latter enters via 140. Inlet chamber 140 is connected to pumping chamber 150 by way of connecting channel 155. Fluid may be collected from a subject through the skin piercing element, into inlet chamber 140, and through connecting channel 155. In certain embodiments, a peristaltic system may be employed to provide a negative pressure on actuation, e.g., a seal may be provided that moves across the membrane 70 of the pumping chamber. In certain embodiments, liquid may flow into chamber 150 partially or solely by inherent liquid pressure. For example, in the embodiments employing a pinch-dispense system described herein, a negative pressure would not be provided upon actuated. Accordingly, in certain embodiments, when actuated, pumping chamber 150 may draw sample from a sampling site of a patient, through the skin piercing element, into inlet chamber 140, and through connecting channel 155. But in any event, pumping chamber transports fluid along the fluidic circuit, e.g., to a sensing chamber.

Pumping chamber 150 may be of suitable geometry. For example, pumping chamber 150 may be convex in geometry. Pumping chamber 150 may have a volume that ranges from about 20 to about 200 nanoliters, e.g., from about 15 to about 150 nanoliters and may have an internal radius that ranges from about 50 to about 1500 microns, and may have an overall length that ranges from about 1000 to about 5000 microns, in certain embodiments.

Figure 5:
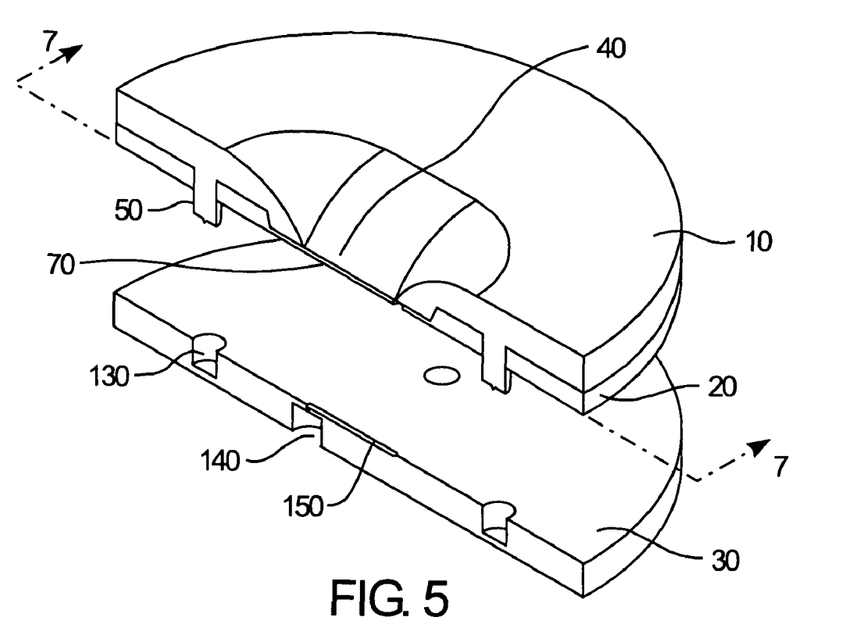
FIG. 5 is perspective, partially assembled view of the fluid handling device of FIG. 1.

FIG. 5 is a partially assembled view of fluid handling device 12, from a first perspective. In this view, pressure disk 10 and elastomeric disk 20 have been joined. Access slot 40 is shown and is in direct proximity to pump membrane 70. Assembly bosses 50 have passed through clearance holes 60, and are aligned for contact with assembly recesses 130. Inlet chamber 140, and pumping chamber 150 are shown as features of sensor disk 30.

Figure 6:
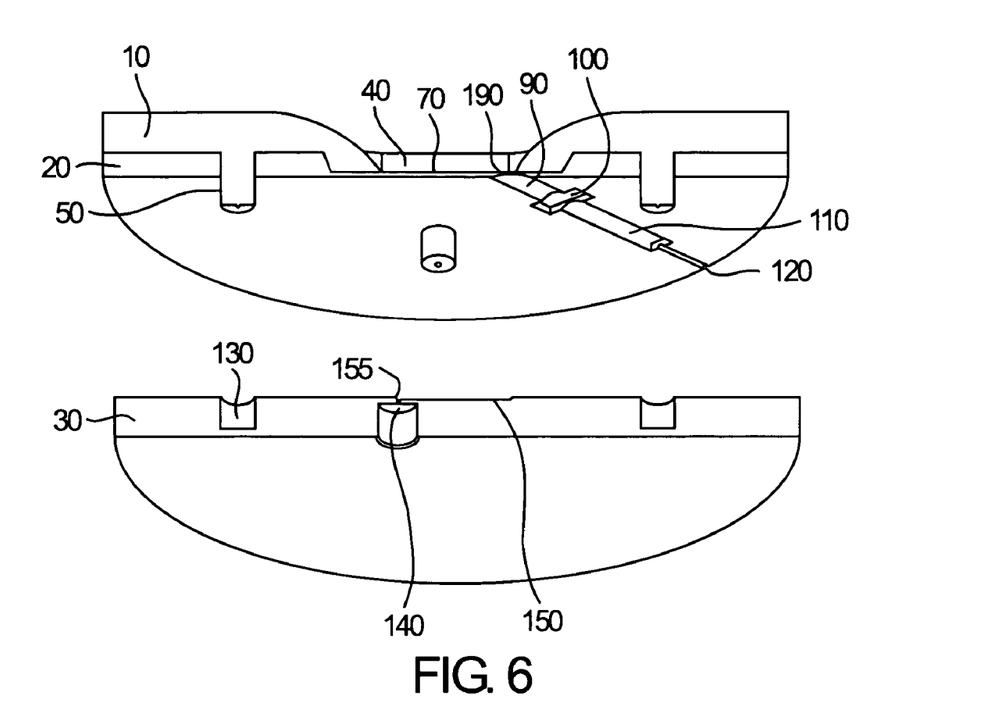
FIG. 6 is another perspective, partially assembled view of the fluid handling device of FIG. 1.

FIG. 6 is a partially assembled view of fluid handling device 12 from a second perspective. In this view, pressure disk 10 and elastomeric disk 20 have been joined. Access slot 40 is shown and is in direct proximity to pump membrane 70. Assembly bosses 50 have passed through clearance holes 60, and are aligned for contact with assembly recesses 130. Inlet chamber 140, connecting channel 155, and pumping chamber 150 are shown as features of sensor disk 30. Inlet channel 90, sensor chamber 100, waste channel 110, and vent 120 are shown in the lower surface of elastomeric disk 20. When assembled to sensor disk 30, inlet channel 90 connects to pumping chamber 150 at channel edge 190. In use, fluid is drawn through a skin piercing element such as a needle (not shown), into inlet chamber 140, through connecting channel 155 and into pumping chamber 150.

In certain embodiments, analyte measurements may be sensitive to flow. In the case of electrochemical glucose measurement, measurements may be sensitive to flow. In certain electrochemically based glucose sensors, glucose is a limiting reactant species. In the case where a glucose measurement is being attempted on a fluid sample that is flowing, glucose is present in excess, and is not a limiting reactant species. This may cause difficulty when correlating current to glucose concentration in the fluid. For this reason, it may be desirable for measurements to be made when the sample has stopped flowing. Flow of sample may be started and stopped by actuating and not actuating pumping chamber 150.

Figure 7:
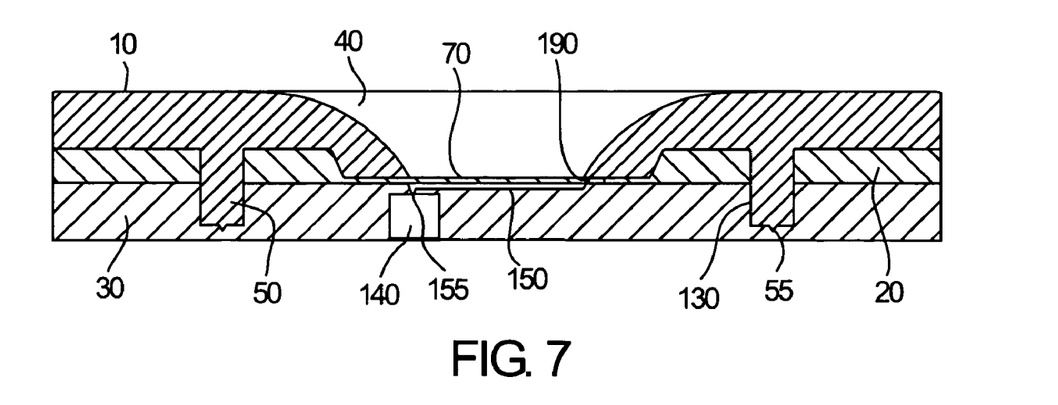
FIG. 7 is a cross sectional view of the fluid handling device of FIG. 1 taken along the section line 7-7 of FIG. 5.

FIG. 7 is a cross sectional view of fluid handling device 12, taken along the section line 7-7 of FIG. 5. In this view, pressure disk 10, elastomeric disk 20, and sensor disk 30 have been assembled. As mentioned previously, in certain embodiments, method of assembly may include ultrasonic welding, with the polymer from the assembly bosses 50 fusing with the polymer from the assembly recesses 130. This may be facilitated by way of concentrated ultrasonic energy and pressure at energy directors 55. When assembled, elastomeric disk 20 is compressed between pressure disk 10 and sensor disk 30. Compression of elastomeric disk 20 against sensor disk 30 seals the edges of pumping chamber 150, inlet channel 90, sensor chamber 100, waste channel 110, and vent 120. As noted above, a skin piercing element such as a sampling needle (not shown) may be connected to inlet chamber 140. Pumping chamber 150 is formed between elastomeric disk 20 and sensor disk 30, with pump membrane 70 forming the top of the chamber. Access to pump membrane 70 by an external actuator is made by way of access slot 40.

Although the embodiment illustrated in FIGS. 4, 5, 6, and 7 use energy directors and ultrasonic assembly, a subject device may be assembled using other methods. For example, certain embodiments may use adhesive. By placing a layer of pressure sensitive or heat activated adhesive between pressure disk 10 and elastomeric disk 20, and between elastomeric disk 20 and sensor disk 30, the three disks may be adhesively joined. Certain embodiments may use external clamping elements to maintain the three components into contact with each other.

One or more other components, which may be integral to the device or separated a distance therefrom, but coupled thereto, such as one or more of, but not limited to, filters, heaters, mixers, and the like, as are well known to those of skill in the art.

As described above, in certain embodiments at least a portion of a fluid pathway includes a sensing chamber 100 (an analytical portion or compartment or reaction chamber) within which processing of a fluid (e.g., analyte detection and/or measurement) may be performed. An analytical portion or compartment or reaction chamber is used herein to refer to a sensor chamber region of a device in which sample processing may be carried out. Examples of functions which may be served by a sensor chamber include, but are not limited to, analyte detection, analyte measurement, chromatographic separations, electrophoretic separations, electrochromatographic separations, and the like.

One type of sensor chamber 100 is photometric or colorimetric or reflectance-type analyte measuring system and in this regard a reaction chamber may be characterized as an optical, calorimetric or photometric reaction chamber. Such sensors may include one or more reagents of a signal producing system, e.g., on a wall of a chamber, that produces a detectable product in proportion to the amount of analyte present in the chamber. The detectable product may then be optically or photometrically detected to provide for a detection of the presence of analyte, and/or a measurement of the concentration of analyte, that is present in the fluid inside the chamber. Such sensors that may be employed in the subject invention include, but are not limited to, those described herein and in U.S. Pat. Nos. 4,935,346; 5,049,487; 5,509,394; 5,179,005; 5,304,468; 5,426,032; 5,563,042; 5,843,692; 5,968,760; 6,743,597; 6,656,697; 6,541,266; 6,531,322; 6,335,203; 6,312,888; 5,563,042; 5,563,031; 5,789,255 and 5,922,530, which are herein incorporated by reference in their entirety.

A signal producing system may be made up of a plurality of reagent components that produce a detectable product in the presence of an analyte of interest. The signal producing system may be an analyte oxidation signal producing system. By analyte oxidation signal producing system is meant that in generating the detectable signal from which the analyte concentration in the sample is derived, the analyte is oxidized by a suitable enzyme to produce an oxidized form of the analyte and a corresponding or proportional amount of hydrogen peroxide. The hydrogen peroxide is then employed, in turn, to generate the detectable product from one or more indicator compounds, e.g., dye couples, where the amount of detectable product produced by the signal producing system, i.e., the signal, is then related to the amount of analyte in the initial sample. As such, certain analyte oxidation signal producing systems may be characterized as hydrogen peroxide based signal producing systems or peroxide producing signal producing systems.

The hydrogen peroxide based signal producing systems may include an enzyme that oxidizes the analyte and produces a corresponding amount of hydrogen peroxide, where by corresponding amount is meant that the amount of hydrogen peroxide that is produced is proportional to the amount of analyte present in the sample. The specific nature of this first enzyme necessarily depends on the nature of the analyte being assayed but is generally an oxidase. As such, the enzyme may be: glucose oxidase (where the analyte is glucose); cholesterol oxidase (where the analyte is cholesterol); alcohol oxidase (where the analyte is alcohol); formaldehyde dehydrogenase (where the analyte is formaldehyde), glutamate oxidase (where the analyte is L-glutamic acid), glycerol oxidase (where the analyte is glycerol), galactose oxidase (where the analyte is galactose), a ketoamine oxidase (where the analyte is a glycated protein, e.g., fructosamine), a 3-hydroxybutyrate dehydrogenase (where the analyte is a ketone body), L-ascorbate oxidase (where the analyte is ascorbic acid), lactate oxidase (where the analyte is lactic acid), leucine oxidase (where the analyte is leucine), malate oxidase (where the analyte is malic acid), pyruvate oxidase (where the analyte is pyruvic acid), urate oxidase (where the analyte is uric acid oxidase) and the like. Other oxidizing enzymes for use with these and other analytes of interest are known to those of skill in the art and may also be employed.

A signal producing systems also includes an enzyme that catalyzes the conversion of a dye substrate into a detectable product in the presence of hydrogen peroxide, where the amount of detectable product that is produced by this reaction is proportional to the amount of hydrogen peroxide that is present. This second enzyme is generally a peroxidase, where suitable peroxidases include: horseradish peroxidase (HRP), soy peroxidase, recombinantly produced peroxidase and synthetic analogs having peroxidative activity and the like. See e.g., Ci et al. (1990) *Analytica Chimica Acta*, 233:299-302.

The dye substrates are oxidized by hydrogen peroxide in the presence of the peroxidase to produce a product that absorbs light in a predetermined wavelength range, i.e., an indicator dye. The indicator dye may absorb strongly at a wavelength different from that at which the sample or the testing reagent absorbs strongly. The oxidized form of the indicator may be the colored, faintly-colored, or colorless final product that evidences a change in color. That is to say, the testing reagent may indicate the presence of an analyte in a sample by a colored area being bleached or, alternatively, by a colorless area developing color. Examples of dye substrates of include, but are not limited to, ANS and MBTH or analogues thereof; MBTH-DMAB; AAP-CTA; and the like. See e.g., in U.S. Pat. Nos. 5,922,530; 5,776,719; 5,563,031; 5,453,360 and 4,962,040; the disclosures of which are herein incorporated by reference.

Another type of sensor chamber is an electrochemical sensing chamber. Various types of electrochemical systems and methods commonly known in the art of analyte detection and measurement may be employed by the present invention, including systems that are amperometric (i.e., measure current), coulometric (i.e., measure electrical charge) or potentiometric (i.e., measure voltage). Electrochemical sensors include an electrochemical cell that includes two electrodes and one or more reagents of an analyte determination system, where these elements work in concert to produce an electrical current in proportion to the amount of analyte present in the chamber. One or more of the electrodes may be an enzyme coated electrode. The generated electrical current provides for a detection of the presence of analyte and/or measurement of the concentration of, analyte that is present in the fluid inside the chamber. Examples of these types of electrochemical measurement systems, which may be adapted for use with the subject invention are further described, e.g., in U.S. Pat. Nos. 6,521,110; 6,475,360; 6,444,115; 6,620.310; 4,224,125; 4,545,382; 5,266,179; 5,834,224; 5,942,102; and 5,972,199; as well as WO 97/18465 and WO 99/49307; and U.S. patent application Ser. Nos. 09/333,793; 09/497,269 and 09/497,304; the disclosures of which are herein incorporated by reference.

As noted above, in certain embodiments sensor 100 located on sensor disk 30 measures an analyte such as glucose electrochemically. The fluid may be interstitial fluid. When measuring an analyte such as glucose, the sensor may contain a redox reagent system that includes an enzyme and redox active compounds or mediators. A variety of mediators are known in the art, such as ferricyanide, phenazine ethosulphate, phenazine methosulfate, pheylenediamine, 1-methoxy-phenazine methosulfate, 2,6-dimethyl-1,4-benzoquinone, 2,5-dichloro-1,4-benzoquinone, ferrocene derivatives, osmium bipyridyl complexes, and ruthenium complexes. Suitable enzymes include glucose oxidase and dehydrogenase (both NAD and PQQ based). Other substances that may be present in a redox reagent system include buffering agents (e.g., citraconate, citrate, malic, maleic, and phosphate buffers); divalent cations (e.g., calcium chloride, and magnesium chloride); surfactants (e.g., Triton, Macol, Tetronic, Silwet, Zonyl, and Pluronic); and stabilizing agents (e.g., albumin, sucrose, trehalose, mannitol and lactose). Other analytes and indicators that may be measured with the sensor include urea, hemoglobin, lactate, alcohol, cholesterol, amino acids, choline, and coagulation factors.

Embodiments include redox reagents systems that may be positioned in any suitable location of a subject device, i.e., in any flow pathway of a device. In certain embodiments, the enzyme component of the reagent may be an enzyme or a plurality of enzymes that work in concert to oxidize the analyte of interest. In other words, the enzyme component of the reagent system may be made up of a single analyte oxidizing enzyme or a collection of two or more enzymes that work in concert to oxidize the analyte of interest. Enzymes of interest include, but are not limited to, oxidases, dehydrogenases, lipases, kinases, diaphorases, quinoproteins and the like. The specific enzyme present in the reaction area depends on the particular analyte for which the electrochemical cell is designed to detect, where representative enzymes include, but are not limited to: glucose oxidase, glucose dehydrogenase, cholesterol esterase, cholesterol oxidase, lipoprotein lipase, glycerol kinase, glycerol-3-phosphate oxidase, lactate oxidase, lactate dehydrogenase, pyruvate oxidase, alcohol oxidase, bilirubin oxidase, uricase, and the like. In certain embodiments in which the analyte of interest is glucose, the enzyme component of the reagent system may be a glucose oxidizing enzyme (e.g., a glucose oxidase or glucose dehydrogenase).

The second optional component of a redox reagent system is a mediator, as referred to above, and which is made up of one or more mediator agents. A variety of different mediator agents are known in the art and include, but are not limited to: ferricyanide, phenazine ethylsulphate, phenazine methylsulfate, phenylenediamine, 1-methoxy-phenazine methylsulfate, 2,6-dimethyl-1,4-benzoquinone, 2,5-dichloro-1,4-benzoquinone, ferrocene derivatives, osmium bipyridyl complexes, ruthenium complexes and the like. In embodiments in which glucose is the analyte of interest and glucose oxidase or glucose dehydrogenase are the enzyme components, mediator of ferricyanid may be employed.

The subject devices may be used in a variety of applications. In certain embodiments, the subject methods are employed in analyte determination assays in which the presence and/or concentration of an analyte in a fluid is determined.

Embodiments of the subject invention provide a number of advantages, including precise control over initiation and/or flow of a fluid in a fluid pathway, where in many embodiments such is achieved automatically. Embodiments of the subject methods include repeatedly (continuously or periodically) obtaining a fluid sample from a subject for analyte determination. Embodiments of the subject invention also include repeatedly stopping and starting flow of fluid in a flow pathway. In this manner, the flow of liquid in a fluidic circuit may be controlled.

In using a subject device, a skin piercing element in contact with the inlet chamber of a fluid handling device is placed in contact with a subject in a manner to pierce the subject's skin to obtain physiological sample. In many embodiments, the skin piercing element is affixed to the inlet chamber or otherwise in communication with the chamber. Fluid is drawn from the subject into the pumping chamber of the device, e.g., by the inherent pressure of the fluid. For example, fluid may be continuously or periodically drawn from a subject during the time period a user-retainable housing is maintained in contact with a body part of the subject, i.e., during the time period the subject wears a device. The fluid present in the pumping chamber may then be transported to a sensing chamber of a device by deflection of the pumping chamber's membrane, as described above. Fluid may be continuously or periodically pumped from the pumping chamber to an analyte sensing chamber, e.g., fresh or new volumes of fluid (e.g., newly collected from a subject) may be continuously or periodically pumped along a fluidic circuit after previously pumped volumes.

Referring to FIGS. 1-7, embodiments of the subject invention include insertion of fluid handling device 12 into local controller 14. This may be performed by a user or fluid handling device 12 may be provided already inserted into controller 14. Local controller 14 is then placed in contact with a user so that sample may be obtained from a site of user. For example, local controller module 14 may be placed upon the arm of a user or the like and retained thereon by a user retainable support.

A skin piercing element of fluid handling device 12 penetrates into the tissue of the user. This may be achieved simply by placing the controller in contact with skin in certain embodiments (i.e., the skin piercing element may extend from the controller so as to penetrate the skin when so contacted).

Communication is established between the local controller 14 and remote controller 16 (if employed), by way of a physical or wireless connection. Controlling commands may be sent between the remote controller 16 and local controller 14. For example, commands such as the timing of the initiation of pumping chamber may be provided, which in turn draws fluid from the user to device 12.

An actuator, e.g., in local controller 14, makes mechanical contact with pump membrane 70 by way of access slot 40. In certain embodiments, a peristaltic type motion may be provided and sample, such as interstitial fluid, may be drawn from the user through a skin piercing element (not shown) and into inlet chamber 140, connecting channel 155, pumping chamber 150, channel edge 190, inlet channel 90, and sensor chamber 100. Representative samples may include, but are not limited to, whole blood and interstitial fluid.

Measurements may then be made by a sensor, located on sensor disk 30 and aligned with sensor chamber 100. Measurements may be made while sample is flowing, or when it is stationary. If it is desired to make measurements while sample is stationary, the actuator may be stopped before measurements are made. To make additional measurements, the actuator may again set in motion, and additional or "fresh" sample may be drawn from the user into the channels and chambers outlined above. Newly drawn sample displaces the previously measured sample. Previously measured sample may accumulate in waste channel 110, while air escapes through vent 120. Alternatively, previously measured sample may be further transported to other sensors of the device for additional measurements of the same or different analyte. This method may be repeated as necessary (drawing sample, measuring, drawing new sample measuring . . . ), and may be part of a broader monitoring method. Broader monitoring methods are described in International Application PCT/GB01/05634 (International Publication Number WO 02/49507 A1), which is hereby fully incorporated herein by reference as noted above.

Results of measurements may be stored in a memory of local module 14 or may be communicated to remote controller module 16. In either case, data may be further processed, e.g., componentry may compare a measurement to a threshold value or other reference value and/or perform computations on the measurement data to provide useful information to a user (or physician) about the state of health of the user such as glucose levels.

In certain embodiments, results of one or more measurements are communicated to the user, physician, or the like, by way of display 406 and/or 508.

Kits

Finally, novel kits are also provided. Kit embodiments may include one or more subject devices which may or may not be already coupled to a local controller module. Accordingly, certain embodiments may include one or more local controller modules for use with a subject device, where a device and a local controller module may be provided coupled or may be provided separated for coupling by a user at a later time. Embodiments may also include one or more remote controller modules.

The subject kits may further include one or more skin piercing elements for obtaining a physiological sample from a subject. A skin piercing elements may be provided affixed to a device or may be provided separated for affixing to a device by a user at a later time. In certain embodiments, a skin piercing element is provided affixed to a device. A plurality of skin piercing elements may be provided in a cartridge for loading into a device.

The subject kits may also include written instructions for using a device and/or local controller module and/or remote controller module for analyte determination. Instructions of a kit may be printed on a substrate, such as paper or plastic, etc. As such, the instructions may be present in the kits as a package insert, in the labeling of the container of the kit or components thereof (i.e., associated with the packaging or sub-packaging) etc. In other embodiments, the instructions are present as an electronic storage data file present on a suitable computer readable storage medium, e.g., CD-ROM, diskette, etc. In yet other embodiments, the actual instructions are not present in the kit, but means for obtaining the instructions from a remote source, e.g. via the Internet, are provided. An example of this embodiment is a kit that includes a web address where the instructions can be viewed and/or from which the instructions can be downloaded. As with the instructions, this means for obtaining the instructions is recorded on a suitable substrate.

In certain embodiments of the subject kits, the components of a subject kit may be packaged in a kit containment element to make a single, easily handled unit, where the kit containment element, e.g., box or analogous structure, may or may not be an airtight container, e.g., to further preserve the integrity (e.g., sterility) of one or more components until use.

It is evident from the above results and discussion that the above described invention provides devices and methods for the determination of an analyte in a fluid. Embodiments of the subject invention provides for a number of advantages including, but not limited to one or more of, ease of use, versatility with a variety of different applications, and the ability to control the flow of fluid in a flow pathway and the ability to control fluid sampling for analyte determination. As such, the subject invention represents a significant contribution to the art.

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An apparatus adapted to measure analytes in bodily fluids of a user, said apparatus comprising:
   (a.) a controller, said controller comprising:
      a motor; and
      an actuator connected to said motor;
   (b) a fluid handling module, said fluid handling module comprising;
      a skin piercing element comprising a fluid collection channel;
      a pressure disk, a sensor disk and an elastomeric disk between the pressure disk and sensor disk;
      the sensor disk comprising an inlet chamber connected to a first end of said fluid collection channel and a pumping chamber;
      a membrane connected to said actuator, said membrane forming at least a portion of one wall of said pumping chamber, said membrane being movable in response to movement of said actuator;
      a connecting channel connecting said collection channel to an inlet end of said pumping chamber;
      the elastomeric disk comprising an inlet channel connecting an outlet end of said pumping chamber to an inlet end of a sensor chamber wherein said sensor chamber includes an electrochemical sensor for detecting said analyte, a waste channel connected to an outlet end of said sensor chamber; and
      a vent connected to an outlet end of said waste channel wherein the apparatus is worn by the user.

2. An apparatus according to claim 1 wherein said analytes comprise glucose.

3. An apparatus according to claim 1, further including a pinching body connected to said actuator.

4. An apparatus according to claim 3, further including a pinch pin adapted to work with said pinching body.

5. An apparatus according to claim 2 wherein said electrochemical sensor utilizes a redox mediator.

6. The apparatus of claim 1, wherein the fluid collection channel is a needle.

7. The apparatus of claim 1, wherein the skin piercing element is affixed to a skin-facing surface of the apparatus for continuous in-dwelling of the skin piercing element in a section of the skin of the user.

8. An apparatus according to claim 1, wherein the pressure and sensor disks are rigid and the elastomeric disk is flexible.

9. An apparatus according to claim 1, wherein the pressure disk further comprises energy directors.

10. An apparatus according to claim 1 or 9, wherein the pressure disk further comprises an access slot suitable to allow the actuator to contact the membrane.

* * * * *

UNITED STATES PATENT AND TRADEMARK OFFICE
CERTIFICATE OF CORRECTION

PATENT NO. : 8,343,074 B2
APPLICATION NO. : 10/883026
DATED : January 1, 2013
INVENTOR(S) : Weidenhaupt et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 234 days.

Signed and Sealed this
Nineteenth Day of March, 2013

Teresa Stanek Rea
*Acting Director of the United States Patent and Trademark Office*